(12) United States Patent
Perry

(10) Patent No.: US 12,264,304 B2
(45) Date of Patent: Apr. 1, 2025

(54) SYSTEMS AND METHODS FOR DEEPWATER PHOTOBIOREACTOR

(71) Applicant: Premium Oceanic Inc., Los Altos, CA (US)

(72) Inventor: Beau G. Perry, San Francisco, CA (US)

(73) Assignee: Premium Oceanic Inc., Los Altos, CA (US)

( * ) Notice: Subject to any disclaimer, the term of this patent is extended or adjusted under 35 U.S.C. 154(b) by 0 days.

(21) Appl. No.: 17/564,814

(22) Filed: Dec. 29, 2021

(65) Prior Publication Data
US 2022/0325215 A1 Oct. 13, 2022

Related U.S. Application Data

(60) Provisional application No. 63/172,407, filed on Apr. 8, 2021.

(51) Int. Cl.
*A01G 7/04* (2006.01)
*A01G 33/00* (2006.01)
(Continued)

(52) U.S. Cl.
CPC ............. *C12M 21/02* (2013.01); *A01G 7/045* (2013.01); *A01G 33/00* (2013.01); *C12M 23/46* (2013.01);
(Continued)

(58) Field of Classification Search
None
See application file for complete search history.

(56) References Cited

U.S. PATENT DOCUMENTS 6,670,169 B1 * 12/2003 Schob ................... C12M 29/08
435/293.1
8,658,420 B2    2/2014 Gorny et al.
(Continued)

FOREIGN PATENT DOCUMENTS

CL     2014002744 A1    4/2015
CL     2023003008 A1    5/2024
(Continued)

OTHER PUBLICATIONS

English machine translation of ES-2652250-T3. Translated on Nov. 9, 2022.*
(Continued)

*Primary Examiner* — Liban M Hassan
(74) *Attorney, Agent, or Firm* — ArentFox Schiff LLP; Christopher Carroll

(57) ABSTRACT

A deepwater photobioreactor system including a vertical stack extending between an ocean surface and an ocean floor. The vertical stack includes an inlet conduit and an outlet conduit where the inlet conduit is arranged to transport at least seawater and the outlet conduit is arranged to transport at least a biomass. The system includes a first photobioreactor in fluid communication with the inlet conduit and the outlet conduit that is connected to the vertical stack via the inlet and outlet conduits at a first position along the vertical stack below the ocean surface. The first bioreactor is arranged to cultivate the biomass. The system also includes a mooring system arranged to anchor the vertical stack to the ocean floor and arranged to receive the biomass via the outlet conduit and output the biomass to a harvest pipeline.

19 Claims, 8 Drawing Sheets

(51) Int. Cl.
*C12M 1/00* (2006.01)
*C12M 1/36* (2006.01)
*C12M 3/00* (2006.01)
*C12N 5/04* (2006.01)

(52) U.S. Cl.
CPC ............ *C12M 29/00* (2013.01); *C12M 41/48* (2013.01); *C12N 5/04* (2013.01)

(56) References Cited

U.S. PATENT DOCUMENTS

| | | | |
|---|---|---|---|
| 8,895,279 B2 | 11/2014 | Burke | |
| 9,376,656 B2 | 6/2016 | Bartilson | |
| 9,816,065 B2 | 11/2017 | Kramer et al. | |
| 9,938,492 B2 | 4/2018 | Gressel et al. | |
| 10,407,653 B2 | 9/2019 | Auner et al. | |
| 2009/0130706 A1* | 5/2009 | Berzin ................. | C12M 23/06 435/257.1 |
| 2010/0216203 A1 | 8/2010 | Trent et al. | |
| 2011/0129906 A1* | 6/2011 | Edelson ................ | C12M 29/06 435/257.1 |
| 2015/0143806 A1 | 5/2015 | Friesth | |
| 2018/0119083 A1 | 5/2018 | Zheng et al. | |
| 2020/0100447 A1 | 4/2020 | Shoham et al. | |

FOREIGN PATENT DOCUMENTS

| | | | | |
|---|---|---|---|---|
| CL | 2023003009 A1 | 5/2024 | | |
| CN | 201245657 Y | 5/2009 | | |
| CN | 102134553 A | 7/2011 | | |
| CN | 109749916 A | 5/2019 | | |
| CN | 110257227 A | 9/2019 | | |
| EP | 2360235 A1 | 8/2011 | | |
| EP | 3659431 A1 | 6/2020 | | |
| ES | 2652250 T3 * | 2/2018 | ............ | C12M 21/02 |
| FR | 2646989 A1 | 11/1990 | | |
| GB | 2469198 A | 10/2010 | | |
| IT | 201900000355 A1 | 7/2020 | | |
| JP | 60-126075 A | 7/1985 | | |
| JP | 2015039316 A | 3/2015 | | |
| KR | 20170073915 A | 6/2017 | | |
| WO | WO-2007011343 A1 * | 1/2007 | ............ | B01D 53/84 |
| WO | 2010/053394 A1 | 5/2010 | | |
| WO | 2010/103154 A2 | 9/2010 | | |
| WO | 2013153402 A1 | 10/2013 | | |
| WO | 2016123077 A1 | 8/2016 | | |
| WO | WO-2017051334 A1 * | 3/2017 | | |
| WO | 2020161711 A1 | 8/2020 | | |

OTHER PUBLICATIONS

English machine translation of KR 10-2017-0073915. Translated on Jun. 11, 2022.*
Nagase et al., "English machine translation of JP 2015-039316A."
Nam et al., "English translation of KR20170073915A."

* cited by examiner

SYSTEMS AND METHODS FOR DEEPWATER PHOTOBIOREACTOR

REFERENCE TO RELATED APPLICATIONS

This application also claims priority to and the benefit of U.S. Provisional Patent Application No. 63/172,407, filed on Apr. 8, 2021, entitled "Photobioreactor Systems and Methods," the entire contents of which are incorporated herein by reference.

TECHNICAL FIELD

This application relates generally to photobioreactors and, more particularly, to deepwater photobioreactors for algae and seaweed cultivation, useful for carbon sequestration, biomaterials and biofuels production.

BACKGROUND

Bioreactors are systems that promote a biologically active environment. A typical bioreactor has a vessel where a chemical process is carried out involving organisms or biochemically active substances derived from organisms. Some common bioreactors have a cylindrical shape. Bioreactors typically operate in one of several modes including a batch, fed batch, or continuous mode, such as continuous stirred-tank bioreactors. Organisms growing in bioreactors are usually submerged in a liquid such as water or sea water. Environmental conditions inside a bioreactor such as temperature, nutrient concentrations, pH, dissolved gases, and light intensity can be controlled. A photobioreactor (PBR) is a type of bioreactor that uses natural or artificial light to enhance the chemical process within the bioreactor. Photobioreactors are often used to grow phototrophic organisms including cyanobacteria, algae, or moss plants. Seaweeds are a group of algae. All seaweed species are autotrophic while some algae species rely on other external food materials. Light provides an energy source via photosynthesis to organisms that can eliminate the need for sugars or lipids as an energy source.

Algae or seaweed biomass produced by a bioreactor can be dried and used as a food for humans. Derived fine biochemical products can be extracted from algae including, for example, cosmetic pigments, fatty acids, antioxidants, proteins with prophylactic action, growth factors, antibiotics, vitamins and polysaccharides. An algae biomass is also useful, in a low dose, to replace or decrease the level of antibiotic in animal food or can be useful as a source of proteins. An algae biomass in wet form can be fermented or liquefied by a thermal process to produce a biofuel. Early photobioreactors used shallow lagoons agitated with one or several paddle wheels. These photobioreactors had poor productivity and were susceptible to seasonal and daily climate variations. They were also confined to tropical and subtropical areas and prone to contamination. Closed cultivating systems address limitations associated with shallow lagoon or open systems by providing more consistent control of environmental conditions such as light, temperature, and culture mixture within the bioreactor. Some bioreactors inject inorganic carbon in the form of gaseous $CO_2$ or bicarbonate as a source of carbon to enhance the growth of microalgae.

Unfortunately, there remains a need for improved algae and seaweed cultivation to increase the quality, efficiency, diversity, and output yield of algae and seaweed producing bioreactors, especially for off-shore and/or deepwater photobioreactors.

SUMMARY

The application, in various implementations, addresses deficiencies associated with cultivating algae and/or seaweed using deepwater and/or off-shore photobioreactors.

A primary purpose of a deepwater photoreactor is to mass produce various algae in a deep column of water. It includes a system designed to operate at very large scale with the benefits of a controlled hyperintensive containment cultivation in an offshore environment. Its applications include supplying food, material and energy markets, as well as solid carbon sources (sCSs). Below a certain depth in the ocean, there is a dramatic shift in temperature and chemistry. Generally, below 100-300 ft across the world's oceans there exists a mixing layer where two chemically and physically discrete volumes of water interact. The deepwater portion is, in much of the world's ocean, a vastly bigger mass. It contains several of the key elements of algal growth, namely nutrients and extremely consistent temperatures. Indeed, the deepwater mass contains an effectively limitless amount of nutrients to which algae are already adapted, but at high concentrations. The temperature range varies in a narrow window of 2-6 degrees Celsius. With endless accessible fertilizer and perfectly stable growing temperatures, the deep ocean invites this innovation.

The missing ingredient in offshore depths is light. As photosynthetic life forms, algae can only survive down to a certain depth. By using an artificial light supplement to drive algal growth, deepwater photobioreactors allow for tapping into the otherwise superb conditions at depth. Beneath the surface layer, the deepwater realm represents 90% of livable space on Earth. It is also, notably, the least biological space on Earth. It can host life but it effectively does not, as compared to the surface and terrestrial habitats. It holds a virtually unlimited and latent feedstock for photosynthesis, with very high levels of nitrogen, phosphorous and dense and diverse micronutrients.

This application describes exemplary deepwater and/or off-shore photobioreactor systems, methods, and devices that more effectively and efficiently cultivate algae and/or seaweed by configuring a bioreactor to optimally stimulate biomass production and/or yield in a deepwater and/or off-shore environment. In various implementations, a deepwater photobioreactor includes an offshore containment vessel for mariculture. The photobioreactor is positioned well below the sea surface with a general maximum depth of at least 100 ft, generally positioned within the richer, cooler deepwater mass. The deepwater photobioreactor features a vertical stack format composed of a combined mooring and conduit system for water delivery and harvested algae.

The deepwater photobioreactor system may include a unique arrangement of flow generators and/or light emitters within the photobioreactor. An optimization of cultivation may be enhanced by monitoring environmental conditions using sensors to provide sensor data to a photobioreactor controller that uses artificial intelligence (AI) and/or machine learning (ML) to process the sensor data while dynamically adjusting operations of various deepwater photobioreactor components to adjust one or more environment conditions within the photobioreactor and, thereby, optimize biomass quality and/or yield or optimize seaweed characteristics for a targeted use. There is an increased need for large scale global seaweed production especially focused on sustainable protein and carbon neutral energy to meet the needs of a climate challenged world. The efficiencies and associated technologies of this application are needed to address the needs of an increased population. A new type of deepwater photobioreactor is proposed to address these unique marketplace challenges.

In one aspect, a deepwater photobioreactor system includes a vertical stack extending between an ocean surface and an ocean floor. The vertical stack includes an inlet conduit and an outlet conduit where the inlet conduit is arranged to transport at least seawater and the outlet conduit is arranged to transport at least a biomass. The system includes a first photobioreactor in fluid communication with the inlet conduit and the outlet conduit that is connected to the vertical stack via the inlet and outlet conduits at a first position along the vertical stack below the ocean surface. The first bioreactor is arranged to cultivate the biomass. The system also includes a mooring system arranged to anchor the vertical stack to the ocean floor and arranged to receive the biomass via the outlet conduit and output the biomass to a harvest pipeline. The system may include a second photobioreactor or more photobioreactors connected to the vertical stack and spaced away from the first photobioreactor.

In one implementation, the first photobioreactor is at least 100 feet below the ocean surface. The vertical stack may include a stack housing positioned at the top of the vertical stack. The stack housing may house or contain at least one pump arranged to move the seawater and/or the biomass through the inlet and outlet conduits. The first photobioreactor may be oriented horizontally. The first photobioreactor may include a vessel configured to provide a unidirectional flow of biomass through the first bioreactor. The first photobioreactor may include a plurality of flow generators oriented to promote unidirectional flow for the biomass through the vessel. Alternatively, the first photobioreactor may include a plurality of flow generators oriented to promote biomass flow from a forward area to aft area of the vessel and a central return system to promote biomass flow from the aft area to the forward area.

The first photobioreactor may include a plurality of light emitters or sources positioned along the unidirectional flow path. The system may include a water turbine arranged to turn in response to water flow and further generate electrical energy to power at least one pump and/or a plurality of light emitters or sources. The plurality of light sources or emitters may include a plurality of LEDs.

In another aspect, a method for cultivating a biomass using a deepwater photobioreactor system includes: extending a vertical stack between an ocean surface and an ocean floor where the vertical stack includes an inlet conduit and an outlet conduit; transporting at least seawater via the inlet conduit; transporting at least the biomass via the outlet conduit; connecting a first photobioreactor at a first position along the vertical stack below the ocean surface where the first photobioreactor is in fluid communication with the inlet conduit and the outlet conduit; cultivating the biomass using the first photobioreactor; anchoring the vertical stack to the ocean floor via a mooring system; receiving the biomass from the outlet conduit at the mooring system; and outputting the biomass to a harvest pipeline.

In a further aspect, a deepwater photobioreactor system includes a vertical stack extending between an ocean surface and an ocean floor, where the vertical stack includes an inlet conduit and an outlet conduit. The inlet conduit is arranged to transport at least seawater. The outlet conduit is arranged to transport at least a biomass. The system also includes a first photobioreactor in fluid communication with the inlet conduit and the outlet conduit. The first bioreactor is connected to the vertical stack via the inlet and outlet conduits at a first position along the vertical stack below the ocean surface. The first bioreactor is arranged to cultivate the biomass. The first photobioreactor includes at least one sensor arranged to generate sensor data based at least on one detected environmental condition. The system includes a mooring system arranged to anchor the vertical stack to the ocean floor. The mooring system is also arranged to receive the biomass via the outlet conduit and output the biomass to a harvest pipeline. The system further includes a controller arranged to receive the sensor data and adjust environmental conditions by at least one of opening, closing, turning on, turning off, adjusting flow rate, adjusting mixing rate of one or more components of the first photobioreactor and/or adjusting light intensity of at least one light source or emitter of the first photobioreactor.

Any two or more of the features described in this specification, including in this summary section, may be combined to form implementations not specifically described in this specification. Furthermore, while this specification may refer to examples of systems, methods, and devices related algae or seaweed producing bioreactors, such techniques also apply equally to bioreactors arranged to cultivate other organisms. For example, the systems and methods described herein related to photobioreactors can be used for any kind of aquaculture such as, without limitation, crustaceans, fish, mollusks, echinoderms, and the like.

The details of one or more implementations are set forth in the accompanying drawings and the following description. Other features and advantages will be apparent from the description and drawings, and from the claims.

DESCRIPTION OF THE DRAWINGS

Like reference numerals in different figures indicate like elements.

DETAILED DESCRIPTION

The application, in various implementations, addresses deficiencies associated with cultivating algae and/or seaweed using photobioreactors. This application describes exemplary systems, methods, and devices that effectively and efficiently implement algae and/or seaweed cultivation in a deepwater and/or off-shore environment by configuring a photobioreactor to optimally stimulate biomass production and/or yield. The optimization may be enhanced by a particular arrangement of flow generators and/or light emitters within the bioreactor. The optimization may be further enhanced by monitoring environmental conditions using sensors to provide sensor data to a bioreactor controller that uses AI and/or ML to process the sensor data and dynamically adjust operations of various bioreactor components to adjust one or more environment conditions within the bioreactor, which optimizes biomass quality and/or yield, or optimizes seaweed characteristics for a targeted use.

Figure 1:
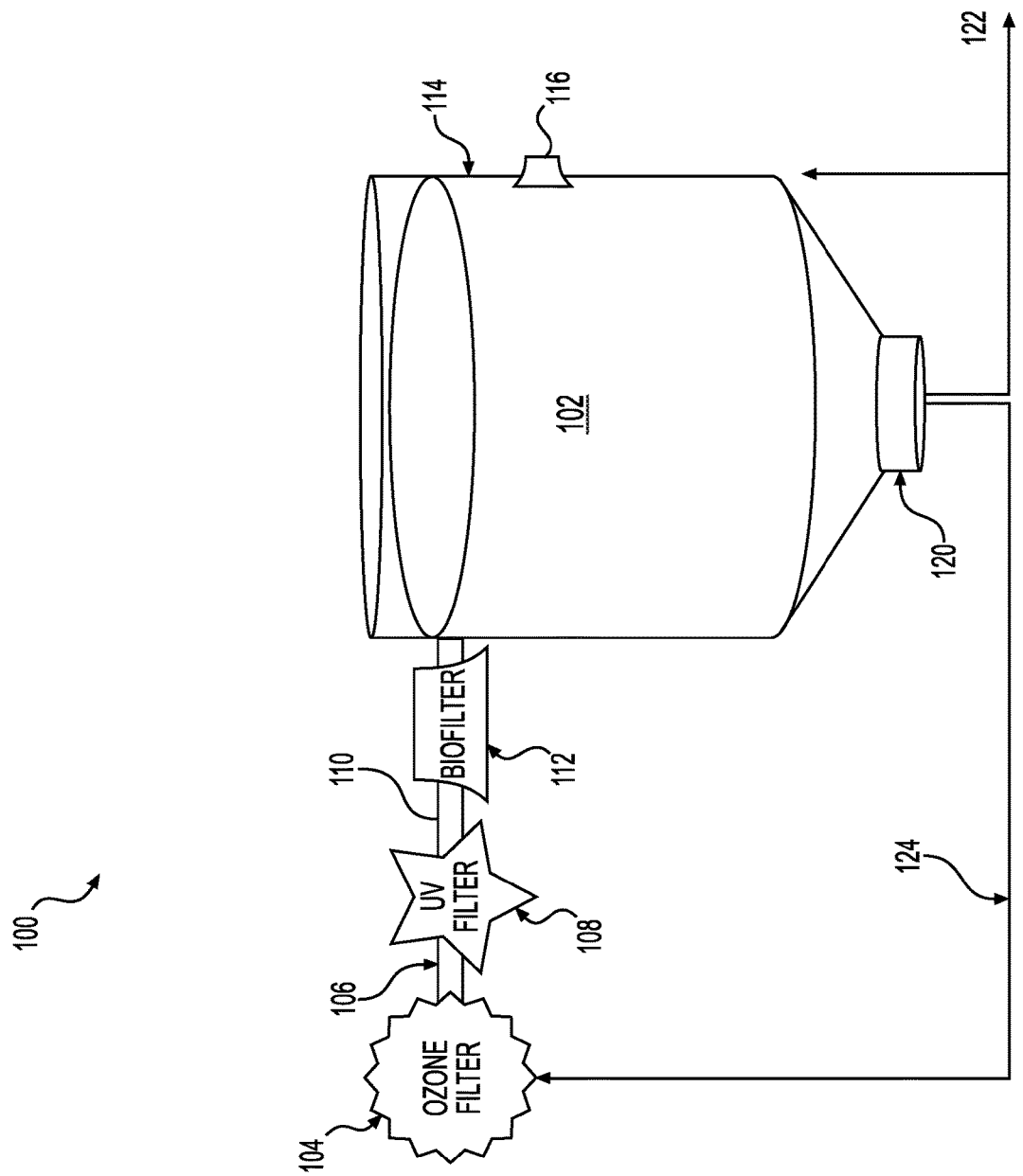
FIG. 1 is a diagram of an exemplary photobioreactor.

FIG. 1 is a diagram of an exemplary of a photobioreactor 100 including a containment structure, vessel, and/or housing 102 which may be implemented in a deepwater and/or off-shore environment or in an on-shore environment. Bioreactor 100 also includes a recirculator 124 connected to a seawater intake 110 having an ozone filter 104, CO2 injector 106, Ultraviolet (UV) filter 108, and biofilter 112. Recirculator 124 and seawater intake 110 provide an input of seawater into containment structure 102 proximate to a top section of structure 102. Seawater intake 110 and/or a dedicated nutrient injector 114 may provide nutrients to a liquid medium, e.g., seawater with or without nutrients, in structure 102. Seawater intake 110 and/or recirculator 124 may use one or more mixing educators to mix liquids from the recirculated liquid from the bioreactor, seawater, nutrients, and other inputs into the containment structure 102. Bioreactor 100 may include one or more environment sensors and/or an array of sensors 116 arranged to sense one or more environmental conditions within bioreactor 100. Bioreactor 100 includes a harvestor 122 arranged to strain seaweed biomass from outgoing water at effluent portal 120 and either reduce the seawater biomass in size that is recirculated back into the containment structure 102 or harvest out a portion of the seawater biomass.

Figure 3:
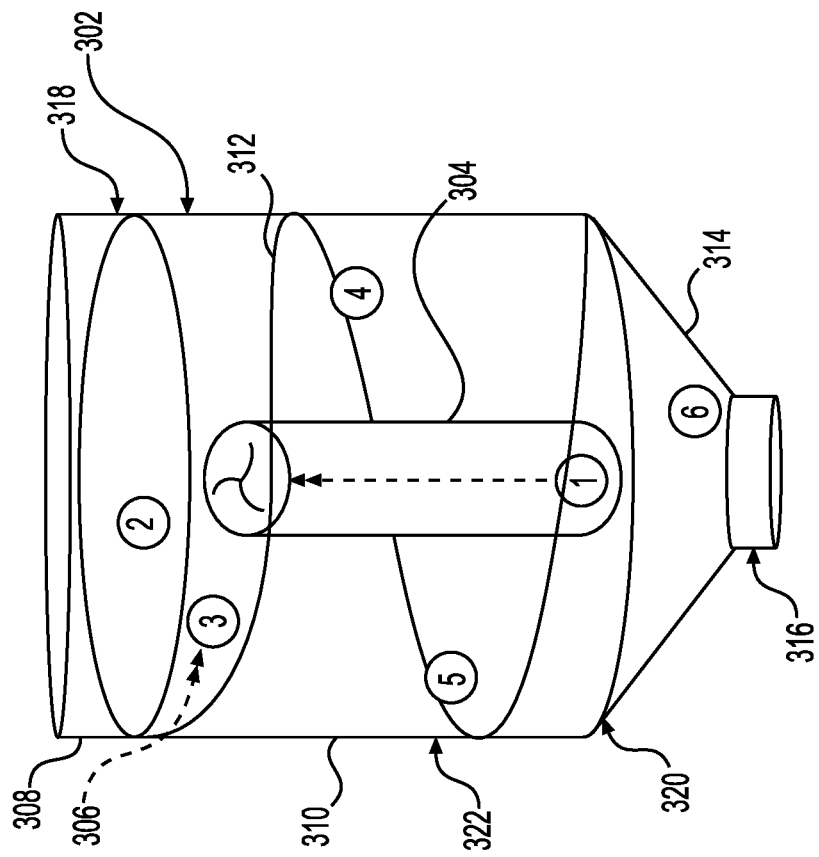
FIG. 3 shows a side view of a photobioreactor.
Figure 4:
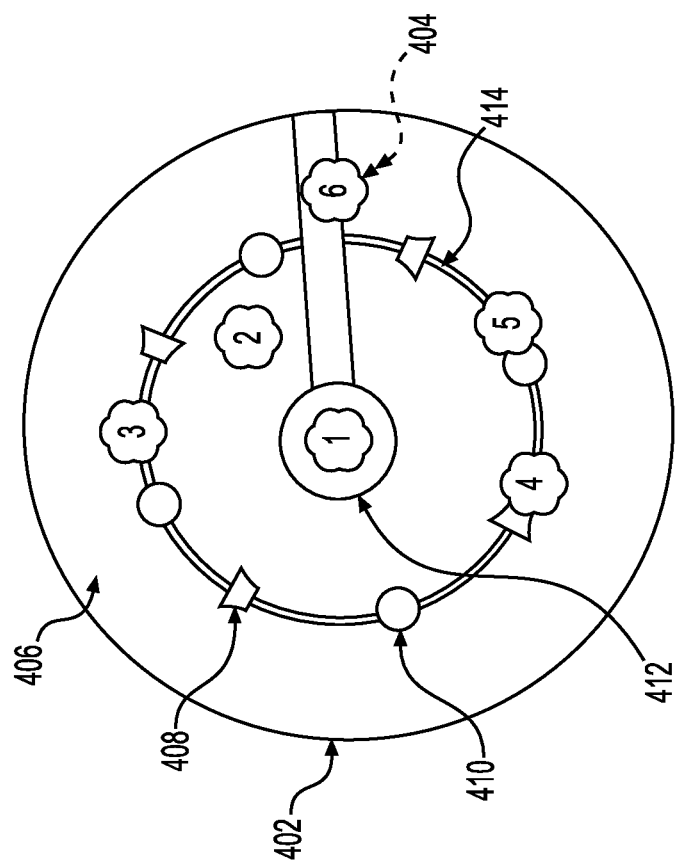
FIG. 4 shows a top-down view of the photobioreactor of FIG. 3.

In some implementations, bioreactor 100 includes a spiral liner positioned adjacent to an inside surface of the at least one sidewall and which is in contact with the liquid culture medium, such as disclosed with respect to FIGS. 3 and 4. In some implementations, bioreactor 100 includes a plurality of flow generators as described with respect to FIGS. 3 and 4, positioned within containment structure 102 in a spiral configuration between the top section and bottom section, arranged to direct a flow of the liquid culture medium from the top section toward the bottom section of containment structure 102.

In certain implementations, bioreactor 100 includes a controller 118 arranged to enable automated control of components of bioreactor 100. Controller 118 may include a processor running artificial intelligence (AI) and/or machine learning (ML), neural networks, Bayesian networks, and/or fuzzy logic to process sensor data received from sensor array 116 and control various environmental parameters of bioreactor 100 including, without limitation, biomass flow rates, temperature, nutrient concentrations, pH levels, dissolved gases concentrations, and/or light intensity. Controller 118 may implement Artificial Neural Networks (ANN) and/or Deep-learning architectures such as deep neural networks, deep belief networks, recurrent neural networks and convolutional neural networks to dynamically adjust environmental conditions within bioreactor 100 or 300. Controller 118 may implement supervised learning, reinforcement learning, and/or unsupervised learning. Reinforced learning may include game theory, control theory, operations research, information theory, and/or simulation-based optimization to dynamically adjust environmental conditions within bioreactor 100 or 300. The bioreactor cultivation environment may be represented as a Markov decision process (MDP). Controller 118 may create multiple decision trees that solve multiple cultivation optimization problems. Controller 118 may use Bayesian networks to optimize an algae and/or seaweed cultivation process.

Controller 118 may use one or more neural networks, such multilayer perceptrons (MLPs), convolutional neural networks (CNNs), or deep Boltzman machines (DBM) that are trained to compute a function that maps an input vector to an output vector. The N-element output vector may convey estimates of the probabilities of N cultivation settings. In some implementations, controller 118 uses a recurrent neural network (RNN) where its neurons send feedback signals to each other to enable dynamic temporal behavior. Controller 118 may use an enhanced RNN referred to as long short-term memory (LSTM) and/or hierarchal temporal memory (HTM). Controller 118 may use a combination of the aforementioned AI algorithms to form a hybrid control system. A decision tree is a generic term that describes a decision process that may use one or more attributes at each node and/or use an information theoretic measure to formulate queries at each node to reach a decision on the optimal cultivation configuration for growing algae and/or seaweed in bioreactor 100.

In operation in one implementation, seaweed and seawater are pumped up through recirculator 124 to top section of containment structure 102, e.g., the top of the liquid culture medium and/or water column. Seaweed reaches surface and begins to sink and spiral back down through the containment structure 102. Seaweed travels along a layer of textile liner while spinning down inside the containment structure and/or silo 102. Seaweed is simultaneously pushed through a spiral conduit and "rotated" by one or more flow generators, e.g, eductors, plumbed into the spiral. Seaweed is exposed to spectrally tuned LED light emitted from light emitters to support or enhance cultivation and/or growth. Heavier biomass and/or other solids are selected out via a vortex of effluent portal 120 for harvest and/or size reduction and/or removal, whereby smaller and/or lighter biomass is sucked into recirculator 124 and pumped back to the top section of containment structure 102. The above cycle repeats continuously during operation.

The diameter or distance between two sidewalls of bioreactor 100 or 300 may be greater than or equal to 0.5 m, 1 m, 2 m, 3 m, 5 m, 7 m, 10 m, 15 m, 20 m, 30 m, 40 m, or 50 meters. The depth or distance from top to bottom of bioreactor 100 or 300 may be greater than or equal to 0.5 m, 1 m, 2 m, 3 m, 5 m, 7 m, 10 m, 15 m, 20 m, 30 m, 40 m, or 50 meters. The containment structure 102 and/or bioreactor 100 may be partially or fully mounted below a ground surface. The containment structure 102 and/or bioreactor 100 may be partially or fully mounted above a ground surface to facilitate more efficient harvesting of biomass. Two or more bioreactors 100 and/or an array of bioreactors 100 may be mounted adjacent to each other to facilitate more efficient biomass harvesting and/or production. The containment structure 102 and/or bioreactor 100 may be partially or fully mounted within a body of water. The containment structure 102 and/or bioreactor 100 may be partially or fully mounted within a body of water periodically, at certain times of day, or during certain tidal events. Light emitters within containment structure 102 may be equally spaced apart horizontally, vertically, and/or circumferentially. Flow generators within containment structure 102 may be equally spaced apart horizontally, vertically, and/or circumferentially. Containment structure 102 may be formed with and/or contain material such as, without limitation, metal (e.g., steel), plastic, concrete, and/or earth materials.

By facilitating a flow of biomass in a downward spiral formation and/or flow path within containment structure 102, bioreactor 100 enables more accurate and efficient detection and/or measurement of biomass flow, volume, and/or yield at a given time or period of time. In some implementations, including a deepwater environment, Bioreactor 100 may be arranged in a substantially horizontal orientation. In such an orientation, one or more eductors may be used to move the biomass in a desired direction, which may or may be assisted by current flow. Bioreactor 100 may include at least one video sensor within containment structure 102. The video sensor may be configured to measure one or more characteristics of the biomass as it flow past the sensor's field of view. The video sensor may provide sensor data to enable a determination and/or detection by, for example, controller 118 of biomass density, distribution, flow, foreign material and/or invasive species. In some configurations, bioreactor 100 includes multiple video sensors positioned along the spiral flow path of the biomass within containment structure 102.

In various implementations, bioreactor 100 operates as a closed and/or on-shore bioreactor. In other implementations, bioreactor 100 operates as a deepwater and/or open bioreactor. There a numerous advantages to operating an on-shore bioreactor including enhanced climate control, control of chemical properties of the liquid culture medium such as nutrient concentrations, and cultivation of types of seaweed tailored for higher value markets. For instance, environmental conditions (e.g., protein and/or sugar concentration) can be adjusted to tailor a seaweed product to a particular use such as for human food, biofuel, animal feed, packaging products, and so on. There are numerous advantages to operating an off-shore and/or deepwater bioreactor including increased production output, use of nutrient rich deepwater, and more efficient cultivation, among other advantages.

Figure 2:
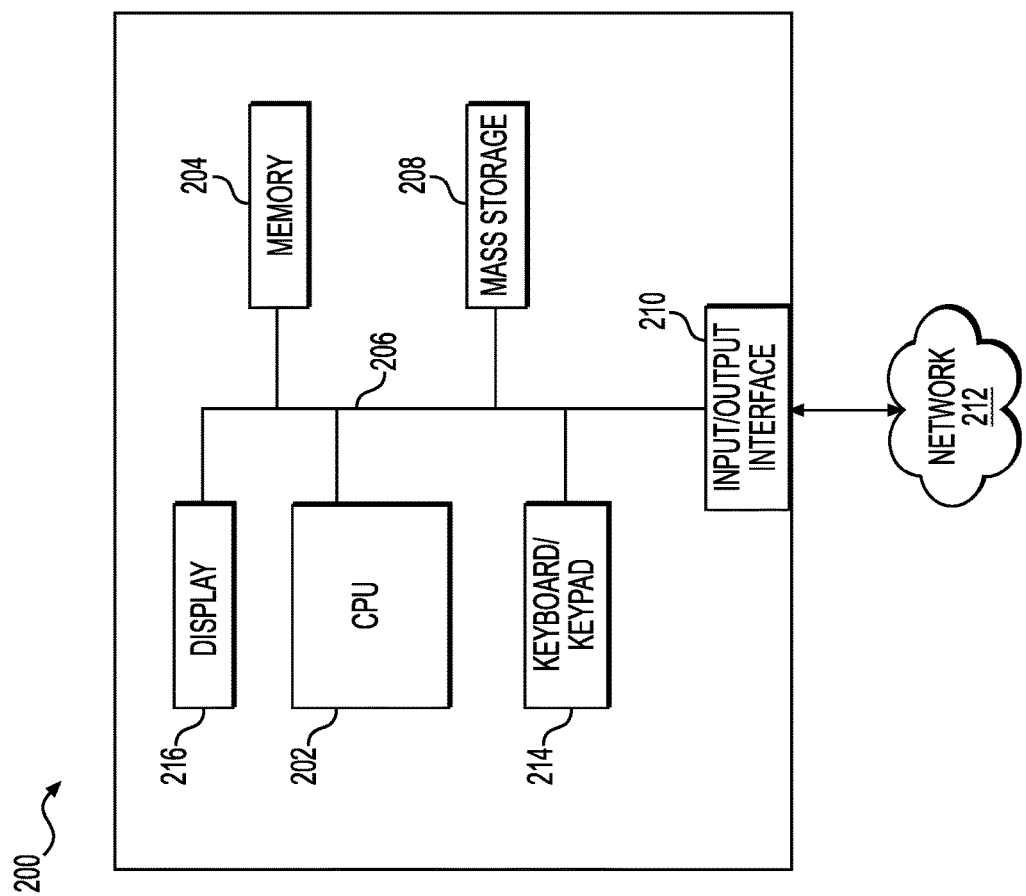
FIG. 2 shows a diagram of a computer system.

FIG. 2 includes a block diagram of a computer system 200 for performing the functions of a computer such as for the controller 118 of FIG. 1. The exemplary computer system 200 includes a central processing unit (CPU) 202, a memory 204, and an interconnect bus 206. The CPU 202 may include a single microprocessor or a plurality of microprocessors for configuring computer system 200 as a multi-processor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 208 may include one or more magnetic disk or tape drives or optical disk drives or solid state memory, for storing data and instructions for use by the CPU 202. At least one component of the mass storage system 208, preferably in the form of a disk drive, solid state, or tape drive, stores the database used for processing sensor data from sensor array 116 and running AI and/or ML engines and/or neural networks for controlling bioreactor 100 or 300. The AI and/or ML engines may implement ANNs and/or Deep-learning architectures such as deep neural networks, deep belief networks, recurrent neural networks and convolutional neural networks to dynamically adjust environmental conditions within bioreactor 100 or 300. To effect automated control of bioreactor 100, 300, 508, 510, and/or 600, or bioreactor system 500, computer 200 may send sensor control signals to various components 104, 106, 108, 110, 112, 114, 120, and 122 of bioreactor 100, 300, 508, 510, and/or 600, or system 500, to either, open, close, turn on, turn off, adjust flow rate, adjust mixing rate, and/or light intensity of light emitters, to optimize algae and/or seaweed production within bioreactor 100, 300, 508, 510, 600, or system 500. The mass storage system 208 may also include one or more drives for various portable media, such as a floppy disk, flash drive, a compact disc read only memory (CD-ROM, DVD, CD-RW, and variants), memory stick, or an integrated circuit non-volatile memory adapter (i.e. PCMCIA adapter) to input an d output data and code to and from the computer system 200. In some implementations, computer 200 and/or controller 118 may control multiple bioreactors concurrently via a data network such as network 212. Controller 118 may coordinate operations among the multiple bioreactors to optimize output production and/or yield among the multiple bioreactors. Network 212 may include a wireless, Adhoc, and/or mobile network, supporting multiple computing servers implementation a cloud computing environment. Various environmental sensors and/or multiple bioreactors may be communicatively connected via network 212 as, for example, Internet-of-Things (IoT) capable systems and/or devices. In some implementations, network 212 may enable computer 200 and/or controller 118 to coordinate operations of multiple photobioreactors by using predictive analytics to process, for example, global position system (GPS) data and other big data to coordinate operations and control of multiple concurrently operating bioreactors over a geographic area. In certain implementations, network 212 may enable collections of, for example, GPS data from multiple bioreactors and use an ML program to enhance security and/or performance for seaweed production on land or in the sea.

The computer system 200 may also include one or more input/output interfaces for communications, shown by way of example, as interface 210 and/or transceiver for data communications via the network 212. The data interface 210 may be a modem, an Ethernet card or any other suitable data communications device. To provide the functions of a computer 102, the data interface 210 may provide a relatively high-speed link to a network 212, such as an intranet, or the Internet, either directly or through another external interface. The communication link to the network 212 may be, for example, optical, wired, or wireless (e.g., via satellite or cellular network). Alternatively, the computer system 200 may include a mainframe or other type of host computer system capable of Web-based communications via the network 212. The computer system 200 may include software for operating a network application such as a web server and/or web client.

The computer system 200 may also include suitable input/output ports, that may interface with a portable data storage device, or use the interconnect bus 206 for interconnection with a local display 216 and keyboard 214 or the like serving as a local user interface for programming and/or data retrieval purposes. The display 216 and/or display 120 may include a touch screen capability to enable users to interface with the system 200 by touching portions of the surface of the display 216. Remote operations personnel may interact with the system 200 for controlling and/or programming the system from remote terminal devices via the network 212.

The computer system 200 may run a variety of application programs and store associated data in a database of mass storage system 208. One or more such applications may include a bioreactor controller 118 that controls various components of system 100, 300, 500, or 600 during the algae and/or seaweed cultivation and/or growth process.

The components contained in the computer system 200 may enable the computer system to be used as a server, workstation, personal computer, network terminal, mobile computing device, and the like. As discussed above, the computer system 200 may include one or more applications that enable cleaning and sanitization of a footwear sole or soles. The system 200 may include software and/or hardware that implements a web server application. The web server application may include software such as HTML, XML, WML, SGML, PHP (Hypertext Preprocessor), CGI, and like languages.

The foregoing features of the disclosure may be realized as a software component operating in the system 200 where the system 200 includes UNIX workstation, a Windows workstation, a LINUX workstation, or other type of workstation. Other operating systems may be employed such as, without limitation, Windows, MAC OS, and LINUX. In some aspects, the software can optionally be implemented as a C language computer program, or a computer program written in any high level language including, without limitation, JavaScript, Java, CSS, Python, PHP, Ruby, C++, C, Shell, C#, Objective-C, Go, R, TeX, VimL, Perl, Scala, CoffeeScript, Emacs Lisp, Swift, Fortran, or Visual BASIC. Certain script-based programs may be employed such as XML, WML, PHP, and so on. The system 200 may use a digital signal processor (DSP).

As stated previously, the mass storage 208 may include a database. The database may be any suitable database system, including the commercially available Microsoft Access database, and can be a local or distributed database system. A database system may implement Sybase and/or an SQL Server. The database may be supported by any suitable persistent data memory, such as a hard disk drive, RAID system, tape drive system, floppy diskette, or any other suitable system. The system 200 may include a database that is integrated with the system 200, however, it is understood that, in other implementations, the database and mass storage 208 can be an external element.

In certain implementations, the system 200 may include an Internet browser program and/or to be configured to operate as a web server. In some configurations, the client and/or web server may be configured to recognize and interpret various network protocols that may be used by a client or server program. Commonly used protocols include Hypertext Transfer Protocol (HTTP), File Transfer Protocol (FTP), Telnet, and Secure Sockets Layer (SSL), and Transport Layer Security (TLS), for example. However, new protocols and revisions of existing protocols may be frequently introduced. Thus, in order to support a new or revised protocol, a new revision of the server and/or client application may be continuously developed and released.

The computer system 200 may include a web server running a Web 2.0 application or the like. Web applications running on system 200 may use server-side dynamic content generation mechanisms such, without limitation, Java servlets, CGI, PHP, or ASP. In certain embodiments, mashed content may be generated by a web browser running, for example, client-side scripting including, without limitation, JavaScript and/or applets on a wireless device.

In certain implementations, system 200 and/or controller 118 may include applications that employ asynchronous JavaScript+XML (Ajax) and like technologies that use asynchronous loading and content presentation techniques. These techniques may include, without limitation, XHTML and CSS for style presentation, document object model (DOM) API exposed by a web browser, asynchronous data exchange of XML data, and web browser side scripting, e.g., JavaScript. Certain web-based applications and services may utilize web protocols including, without limitation, the services-orientated access protocol (SOAP) and representational state transfer (REST). REST may utilize HTTP with XML.

The system 200 may also provide enhanced security and data encryption. Enhanced security may include access control, biometric authentication, cryptographic authentication, message integrity checking, encryption, digital rights management services, and/or other like security services. The security may include protocols such as IPSEC and IKE. The encryption may include, without limitation, DES, 3DES, AES, RSA, and any like public key or private key based schemes.

FIG. 3 shows a side view of photobioreactor 300 including a recirculator and/or return system 304 within its containment structure 302. While FIG. 3 shows photobioreactor 300 in a vertically align orientation, photobioreactor 300 may be aligned in other orientations including, for example, a horizontal or substantial horizontal orientation. Containment structure 302 forms a cavity in which a liquid culture medium 310, e.g., a seawater growing medium, is contained. Recirculator and/or medium return system 304 forms a channel within containment structure 302 including an inlet proximate to bottom section 320 and outlet proximate to the top section 318. Recirculator 304 includes a pump arranged to continuously receive a portion of liquid culture medium 310 via the inlet in bottom section 320 and output the portion of liquid culture medium 310 via the outlet in top section 318. Recirculator 304 may be position centrally to contribute to a downward spiral flow path 306 of biomass and/or medium 310 within containment structure 302. When photobioreator 300 and containment structure 302 are horizontally aligned, recirculatory 304 returns biomass to the section 318 while one or more eductors may push portions of the biomass along a spiral path toward section 320. When photobioreactor 300 is oriented horizontally, section 318 may be referred to a forward section 318 and section 320 may be referred to as aft section 320.

Bioreactor 300 also includes a spiral liner 312 adjacent to an inner surface of sidewall 322 of containment structure 302. The spiral liner 312 enables, at least partially, a downward spiral flow path for seaweed 306 from a section 318 toward section 320 of containment structure 302. When bioreactor 300 is oriented vertically, gravity and/or one or more flow generators may also assist in providing a downward spiral flow of biomass and/or medium 310 within containment structure 302. When bioreactor 300 is oriented horizontally, ocean current and/or one or more flow generators may assist in providing forward-to-aft or aft-to-forward spiral flow of biomass and/or medium 310 within containment structure 302. Bioreactor 300 may also include a vortex grading and draining funnel 314 arranged to enable harvesting of seaweed biomass via effluent portal 316. Containment structure 302 may have a sealed section 318 arranged to enable a gas layer 308 above the liquid culture medium 310. Although not shown in FIG. 3, bioreactor 300 may include one or more components as described with respect to bioreactor 100 of FIG. 1. For example, bioreactor 300 may include an array of sensors, one or more lights emitters, and/or a controller such as controller 118 of FIG. 1. Bioreactor 300 may be configured to operate as an on-shore and/or closed system or operate as a deepwater, off-shore and/or open system within a body of water such as the ocean. When operating as an on-shore or closed system or as a deepwater system, bioreactor 300 may include a recirculator such as recirculator 124 of FIG. 1 in addition to or alternatively to recirculator 304.

FIG. 4 shows a top-down view 400 of photobioreactor 300 of FIG. 3 when photobioreactor 300 is arranged in a vertical orientation. FIG. 4 also provides an inline or axial view of photobioreactor 300 when photobioreactor 300 is in a horizontal orientation. FIG. 4 includes silo containment structure 402, spiral liner fabric 406, multiple eductors 408, multiple marine light emitters (e.g., LEDs) 410, return column 412 of recirculator 304, and an educator, electrical, and/or drainage conduit 414. FIG. 4 shows a downward spiral flow 404 between return column 412 and spiral liner fabric 406. In certain implementations, flow generators (e.g., eductors 408) and/or light emitters 410 are spaced horizontally, vertically, and/or circumferential equally or substantially equally apart. By arranging multiple light emitters along a vertical depth and/or horizontally at various depths, the vertical length of bioreactors 100 or 300 can be extended substantially with respect to conventional bioreactors that rely on natural sun light. Conventional bioreactors are typically limited to about a 2.5 m depth due to limited penetration of natural light through a cultivating medium via the top of a conventional bioreactor.

By positioning multiple light emitters at various depths and/or along the downward spiral flow path 404 or 306 of medium 310, an exposure of medium 310 to energy provided by light is substantially enhanced to, thereby, increase biomass yield and/or a consistency of the seaweed biomass product. This is another technical advantage of implementing a downward spiral flow path 404 or 306 within bioreactor 300 and/or 100. As discussed with respect to FIG. 1, eductors 408 and/or flow generators may be oriented in a downward direction toward bottom section 320 but also oriented in horizontal direction to encourage the spiral downward flow 404 and 306. In some implementations, eductors 408 and/or flow generators are oriented and/or positioned to promote medium flow 404 and/or 306 in a parallel or substantially parallel direction as spiral liner 312. Eductors 408 may have a vertical orientation less than or equal to 2, 5, 10, 15, 20, 30, or 45 degrees from horizontal in a downward direction toward bottom section 320 and/or effluent portal 316 or 120.

Figure 5:
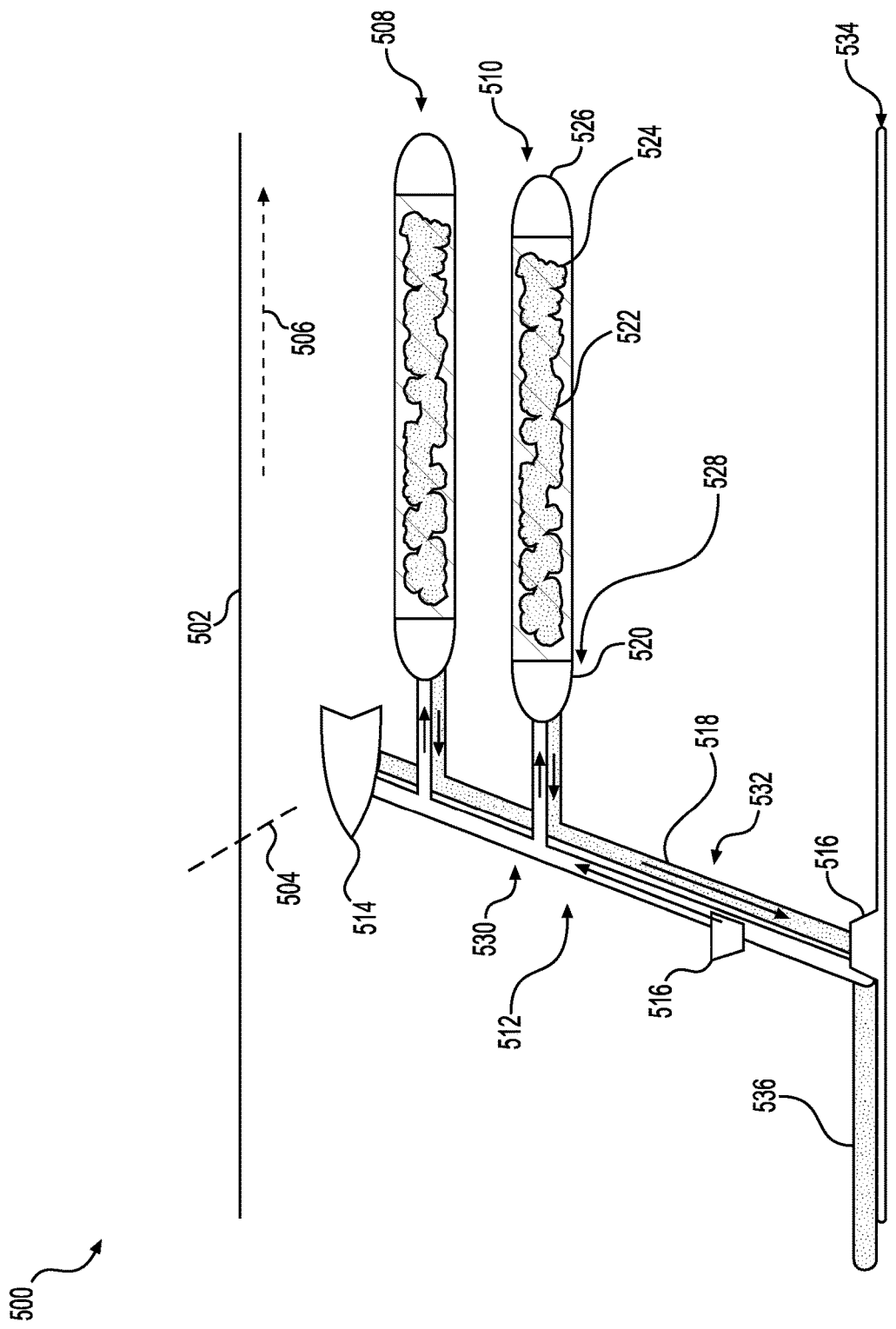
FIG. 5 shows a deepwater photobioreactor system including multiple photobiorectors.

FIG. 5 shows a deepwater photobioreactor system 500 including multiple photobiorectors 508 and 510. Each deepwater photoreactor 508 and 510 includes an offshore containment vessel for mariculture. System 500 includes a surface conduit 504, stack 512, stack housing 514, photobioreactor and/or vessel 508, photobioreactor and/or vessel 510, harvest pipe 536, intake conduit 530, outlet conduit 532, and mooring system 516. A photobioreactor such as photobioreactor 510 may include a forward housing and coupling 520, adjustable intake or dumb waiter 528, corkscrew textile liner 522, and aft housing and return system 526.

System 500 is positioned below the sea surface 502 with a general maximum depth of at least 100 ft. In some implementations, the depth of the most shallow bioreactor 508 is at least 100 ft, 200 ft, 300 ft, 500 ft, 1000 ft, 2000 ft, and 5000 ft. System 500 is generally positioned within the richer, cooler deepwater mass. System 500 features a vertical stack 512 format composed of a combined mooring 516 and conduit system including an inlet conduit 530 for water delivery and an outlet conduit 532 for harvested algae. Surface conduit 504 may enable electronic communications and/or transport of materials to or from stack housing 514. Surface conduit 504 may be permanent or temporary.

One advantage of positioning system 500 under the ocean surface 502 is that system 500 provides a depth feature that is valuable in eliminating surface navigation and reducing wildlife interaction hazards. It also mitigates fouling, as there is less life below the photic zone and much less so below the mixed layer of the ocean. A key technical advantage of the deepwater system 500 is the ability to create a quarantine zone, especially in tropical waters where the crop will be adapted to very cold temperatures but the surface waters may be greater than 15 degrees Celsius (C). Because deepwater crops are far from any surface light and have negative buoyancy, such crops would not be able to survive if they did reach the surface. Hence, system 500 produces a biologically isolated, i.e. quarantined biomass. The use of non-native species and genetically modified organism (GMO) strains create far less risk in this context.

The system 500 vertical stack 512 may be moored to the seafloor 534 and be connected to and/or include a pair of large-diameter conduit pipes, e.g., high density polyethylene (HDPE) pipes, running between the seafloor and the stack housing. One conduit 530 may be for a water supply, the other conduit 532 for harvested material to transit either to a seafloor pipe 536 or a surface vessel. Stack 512 may include additional sub-conduits having electrical and data cabling, and can be used to deploy interior drones to monitor system 500 and/or deliver fluids (e.g., for decontamination, CO2-enhanced materials, nutrients, probiotics) to clean and maintain both the conduits 530 and 532 and the containment vessels of photobioreactors 508 and 510.

The top of stack 512 may include a stack housing or cap 514 that includes an upper terminus for the two pipes 530 and 532. Positioned at the top of the overall system 500 and being most accessible to the surface, stack housing 514 may serve as a pump house to move water and/or materials within the two pipes 530 and 532. Stack housing 514 may include a computing and/or communications center, e.g., computer 200, robot housing, parts and a materials warehouse. The stack cap or housing 514 may be connected to a surface buoy which provides data uplink and allows surface vessels to locate and dock with the vertical stack 512 and/or system 500 to service the stack 512 by, for example, supplying parts and materials, maintenance/repair, seeding, surface harvest, and so on. In some configurations, stack 512 can be decoupled and brought to the surface for repair or replacement.

The mooring base 516 can also include a house pump, filtration, house parts and robots. Mooring base 516 may link the harvest pipe 532 to a seafloor pipeline 536 which may be linked a series of stacks and/or photobioreactor systems. Hence, multiple systems 500 may be linked together via one or more seafloor pipelines to enable collection from each system and transport of a consolidated material stream to an endpoint which may be located on-shore or at an off-shore collection point. The two vertical conduits 530 and 532 may include respective ports at regular intervals along stack 512 to either feed seawater into or draw material (plus water) from the containment systems of photobioreactors 508 and 510. The intake conduit 530 can draw external seawater in at least one of two ways, either via an intake port using pumping, or passively absorb it by using micro-perforations in the conduit material itself. Or implement a combination thereof. Filtration may be provided by the micro-perforated pipe and/or integrated in the active intake system. The micro-perforation of pipe 530 can be at intervals with the ability to cover or block individual micro-perforated sections.

The active pumped intake system's depth may be adjustable either by having multiple intake ports along the length of intake conduit 530, and/or by covering or opening the micro-perforated sections of conduit 530. The adjustability of intake depth allows system 500 to draw the right mix of water from the right depths to ensure an optimal water temperature, nutrient levels and/or general intake quality. For example, water may be drawn at deeper depths to obtain cooler water and drawn at shallower depths to obtain warmer water. Pumps within the stack housing 514, the intake conduit 530, and the mooring system 516 may be controlled, via a controller such as computer 200, in a cooperative manner to ensure the proper mixing and distribution of water within the intake conduit 530 to supply the containment vessels 508 and 510.

In some implementations, system 500 may be compatible with an ocean thermal exchange system, which is fundamentally similar to the two intake/harvest conduits except that it directly loops the two pipes to create a continuous flow. An ocean thermal energy conversion (OTEC) system may be added to system 500 to provide the electricity for system 500, by using temperature differentials between deep water and surface water (especially tropical waters). This differential is also useful in conditioning water temperatures within the intake conduit 530, i.e., by taking water with ideal nutrients at one depth and/or temperature and running it to another depth to cool or warm it to the optimal temperature within the intake pipe 530.

The photoreactor containment vessels of photobioreactors 508 and 510 may have cylindrical lengths of fabric designed to host the ongoing cultivation of a biomass with continuous harvest. In some implementations, they are made of low-cost high-durability material that hold in the biomass and the seawater delivered from the intake conduit 530 and keep out exterior seawater and organisms. The vessel of photobioreactor 508 or 510 may include a loop wherein nutrient-rich intake water is delivered to the interior, run through the biomass, and the spent water is expelled along with the harvested material via conduit 532.

A containment vessel may include as few as a pair of parallel containment lengths or be grouped as multiple parallel containments with the groupings either being pairs or one interconnecting piece running back and forth in an "intestinal" configuration. Each photoreactor 508 and 510 containment may have an intake seawater delivery system with a pump at an entry point where it is connected to the conduits, and piped into the vessel interior via a series of pressurized flow generator or eductor nozzles throughout the vessel interior to maintain a unidirectional overall flow of biomass plus optimal distribution of the biomass for maximum access of each organism to both light and seawater. The intake port connecting the containment vessel to the intake conduit can be used primarily for filling (e.g. after installation) or flushing the vessel, whereas the distributed water delivery system plumbed along the system interior supplies cultivation. The plumbing runs the flow generators and/or eductors along the bottom of each containment in order for the eductor flow energy to work to push the biomass both upwards (since they are negatively buoyant) and onwards in its unidirectional and evenly-distributed course through the photobioreactor when operating the vessel of a photobioreactor 508 and 510 with positive pressure.

The even and unidirectional flow of biomass allows the material to be fully gated through a series of monitoring systems (e.g., photosensors) and growing conditions, e.g., photoperiod regimes, with highly accurate data and precise physical control throughout. The flow generators and/or eductors can be dynamically adjusted via a controller, such as computer 200, to control the biomass speed, distribution, and nutrient levels because the eductors are both delivering physical force along with the seawater intake. Temperature can be controlled and/or influenced also by the intake water.

Each vessel of photobioreactors 508 and 510 has a harvest port adjacent to the intake port, connecting as an outfall connecting to the harvest conduit 532. Sensors identify approaching biomass and a controller dynamically adjusts water flow and pressure to select out the material for harvest the conduit 532. The controller may control system functions to separate the less viable biomass for harvest, while returning the healthiest and most robust material back into the loop within the vessel of bioreactor 508 or 510. Sensors may detect via optical, mass spec, sonar, and so on, the size of individual pieces, their chemical signature, their density, presence of other organism, and so on, to determine which are viable and which should be harvested, while continuously adjusting pump flows between the approaching set of eductors and the harvest pump to cull or "kick out" the desired material into the harvest pipe 532, including the purge of any foreign organisms and materials. In some implementations, density will be a key factor in separating harvest out, whereby cyclonic force can "centrifuge" the lighter material from the heavier. This may become an ongoing genetic selection program in which the genomes which adapt best to the conditions are those which are kept in cultivation, and those which do not are harvested. The harvesting selection mechanism and approach has the potential to foster the evolution of improved strains, which can be sampled and recovered for general seed development purposes. A successful biomass may be transplanted from one vessel 508 to seed or supplement another vessel 510 in the stack 512.

A size-reducer (e.g., blender) can be used within the harvesting and/or return mechanism within conduit 532 and/or the forward housing and coupling 520 to ensure optimal size of biomass particles in either the returned biomass and/or harvested material. For the returned biomass, smaller pieces tend grow faster and distribute better. In the harvested material, smaller particles pump faster and at higher density. In both cases, size uniformity is also highly useful. Further "seive-ing" the outgoing harvest material can dewater the contents to increase and/or adjust density of biomass 524 going into the harvest conduit 532 to a specific level.

The interior of vessel 508 or 510 may be white for maximum reflective purposes with lighting distributed to supply the biomass 524 with the energy for photosynthesis. The use of waterproof LEDs with adjustable intensity and spectra allows for fine control of photosynthetic activity, done automatically by AI/ML in conjunction with sensors and monitoring equipment via, for example, a controller such as computer 200. Growth can be increased or decreased in this solution by the controller dynamically adjusting light intensity, photoperiod, and/or spectrum. The interior structure of vessel 508 or 510 features a fabric spiral which is used to corral and optimally distribute biomass 524 along its unidirectional course, and keeps it exposed to the optimal light, i.e., ensuring any given piece or portion of biomass 524 is never too far from access light for too long. By increasing the surface area with a material that also helps to organize and direct the biomass 524, this creates space for additional lighting fixtures that better penetrate into the center of a vessel 508 or 510.

The exterior of a vessel 508 or 510 may be black to minimize light and the attraction of organisms which might foul or otherwise interfere with system 500. Robots may assist in the operation of the system 500, working internally within the conduits such as conduits 530 and 532, and vessel containments such as vessels 508 and 510, as well as external to the system 500. They may be able to charge via, for example, magnetic wireless charge points and/or strips and data link within the entire system 500 using acoustic or other short-range wireless protocols. The eternal robots can include a "smart-waiter" 516 which can run up and down the length of the conduits 530 and 532 either on a track or by other means, with the ability, e.g., arms/tools, to clean and maintain the system 500. The containment vessels 508 and 510 may include external tracks or rails for robots to inspect and service them.

In some implementations, the photoreactor system 500 includes an automated system having a controller running on an upgradable AI/ML computing application, able to operate autonomously and with full-time satellite data connectivity. Stack 512 fleets may then be operated as a networked fleet via the controller and/or software. Not only does this system learn and improve in real time, it yields insight for future hardware improvements. Electrical energy can be delivered externally to system 500 via, for example, an offshore wind or grid connection, or it can integrated via current or OTEC systems to provide a native energy supply, either as part of each stack 512, or via centralized power source within a fleet of stacks 512.

The conduit 530 or 532 and containment vessel 508 or 510 segments can be standardized, i.e., formatted and sized to accommodate the most efficient delivery and installation of the hardware packaging, e.g., for rail and/or shipping. The conduits may each include of a series of pipe sections that can be connected during installation, and each section can be removed and replaced as necessary. Each containment vessel 508 or 510 has potential applications for not only algae but also rearing production of fauna, e.g., fish, shrimp, shellfish, and the like. While not photosynthetic, these organisms may benefit from certain lighting features. As a multi-trophic aquaculture platform, individual vessel 508 and 510 containments can contain different species, and algal outfall water can be rerouted into fauna vessels to provide higher-PH water for improved rearing conditions of, for example, shellfish. Fauna waste can also be routed into seaweed cultivation as fertilizer for remediation of effluent.

In some implementations, photoreactor system 500 includes a solar system located at the top of the water column and/or stack 512 that is floating on the surface 502 to collect sunlight for the photosynthesis of algae. System 500 may still include artificial lighting as an enhancement. System 500 may include water transport systems, e.g., pumps and conduits, with the ability to draw up cooler, more nutrient-dense water from a determined depth to support optimal yield.

Figure 6:
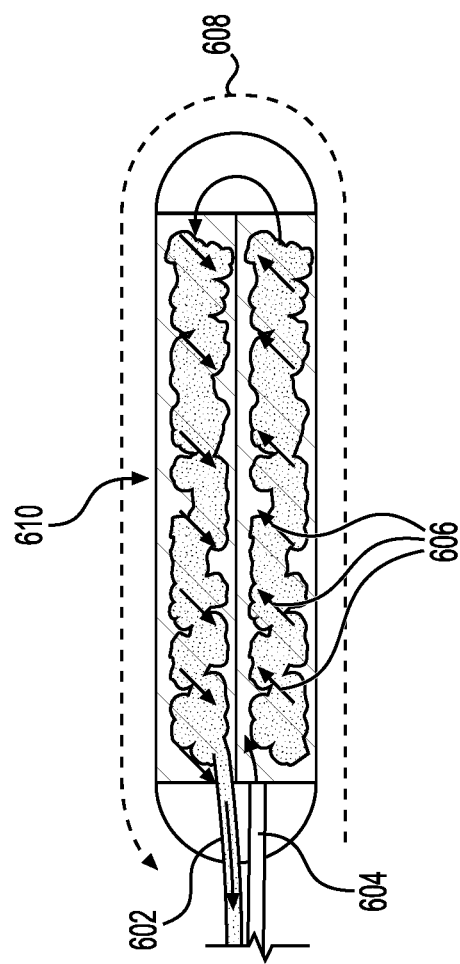
FIG. 6 is a top down view of a photobioreactor of FIG. 5.

FIG. 6 is a top-down view of a photobioreactor 600 such as photobioreactor 508 or 510 of FIG. 5. Photobioreactor 600 includes a containment vessel 610, harvest outlet and/or pipe 602, seawater intake and/or pipe 604, and multiple flow generators and/or eductors 606. In the implementation shown in FIG. 6, photobioreactor 600 is arranged to provide a unidirectional flow path 608 of seawater and biomass through vessel 610. The multiple flow generators 606 are spaced along the wall of vessel 610 and oriented to enable the flow of biomass along path 608 from the intake 604 and toward the harvest outlet 602. The implementation of FIG. 6 includes at least two columns in parallel that provide a flow path 608 through the vessel 610. In some implementations, more than two column and/or channels may be used. In an alternate implementation, photobioreactor 600 and/or vessel 610 may be configured to provide biomass flow like systems 100 and 300. In the configuration of FIG. 6, various components as described with respect to systems 100 and 300 may be implemented in photobioreactor 600 including, for example, the use of multiple light emitters/sources and flow generators.

Figure 7:
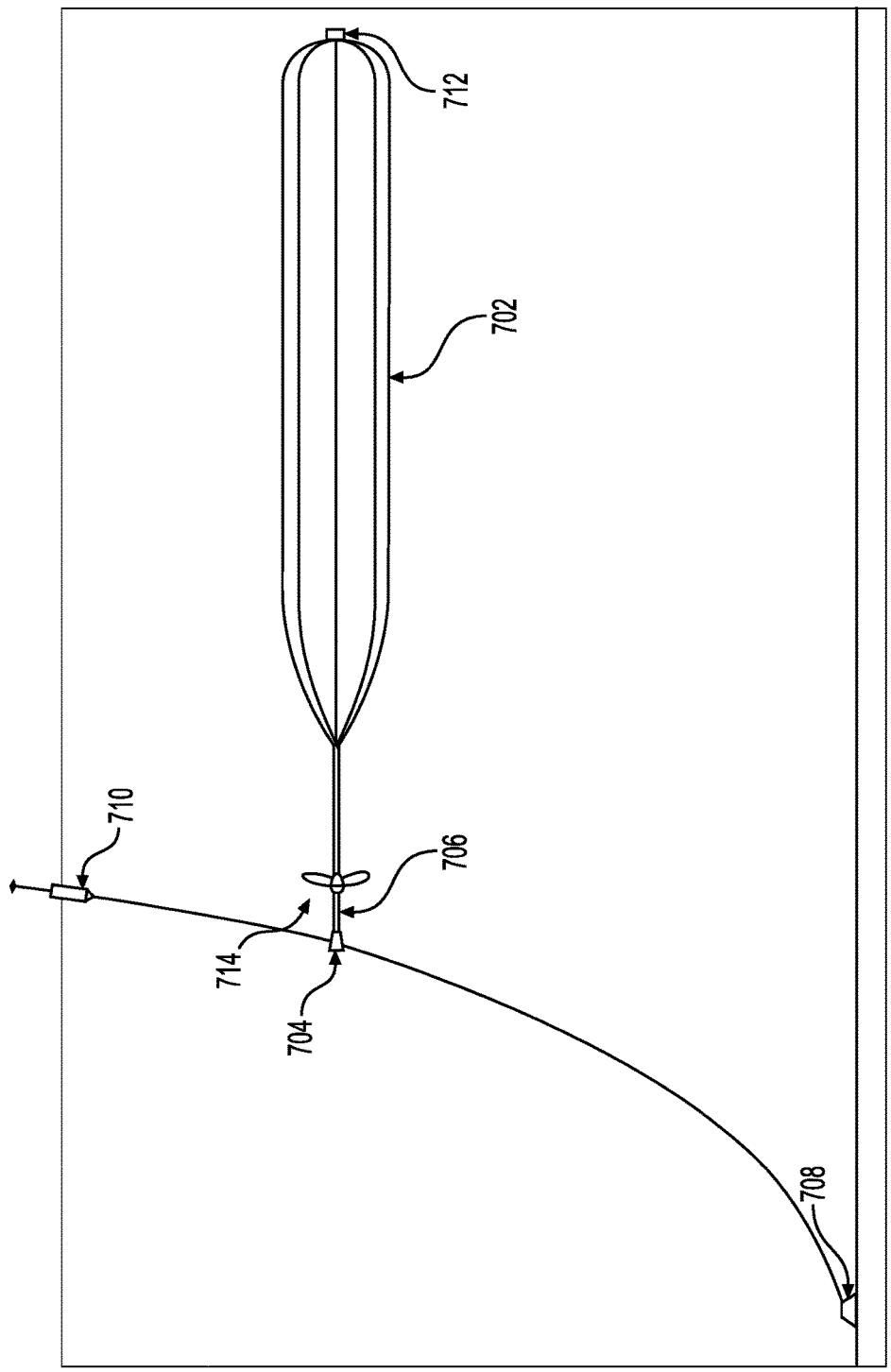
FIG. 7 shows another photobioreactor system.

FIG. 7 shows a photobioreactor system 700 including a neutrally buoyant photobioreactor 702 having a photobioreactor intake 706, a water turbine 714, and a screened exit port 712. System 700 includes an omni-directional anchor 708, an intake for nutrient rich seawater 704, and a surface buoy 710. Turbine 714 is arranged to turn in response to seawater flow across its turbine blades that turn generator coils to generate electrical energy that may be used to power any component that needs power including, for example, a controller, one or more conduit pumps, one or more flow generators, and/or light emitters within photobioreactor 702. Surface buoy 710 may provide depth control for system 700 and/or photobioreactor 702. Photobioreactor 702 may include buoyant material to enable neutral buoyancy and/or fixed flotation in the water. In operation, nutrient rich seawater is received by photobioreactor 702 via intakes 704 and 706. Photobioreactor 702 may include a unidirectional flow path that extends from a forward area next to intake 706 toward an aft area adjacent to screened exit port 712. The screen of screen exit port 712 may provide a filter function to only allow harvesting of biomass of a selected size.

Figure 8:
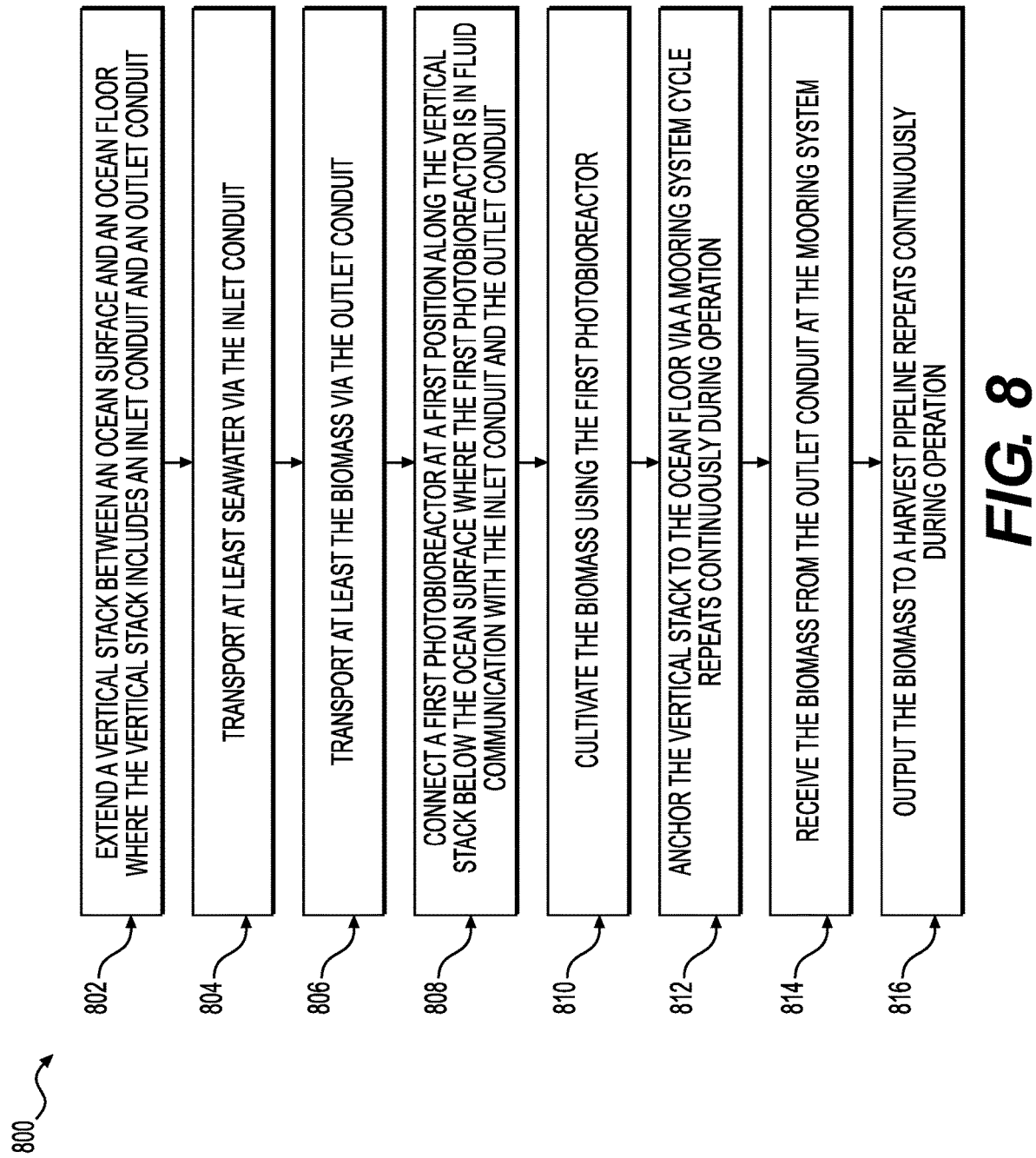
FIG. 8 illustrates a seaweed cultivation process related to the operation of the photobioreactor of FIG. 5.

FIG. 8 illustrates a seaweed cultivation process 800 related to the operation of the photobioreactors 508 and 510 of FIG. 5. Process 800 includes: extending a vertical stack between an ocean surface and an ocean floor where the vertical stack includes an inlet conduit and an outlet conduit (Step 802); transporting at least seawater via the inlet conduit (Step 804); transporting at least the biomass via the outlet conduit (Step 806); connecting a first photobioreactor at a first position along the vertical stack below the ocean surface where the first photobioreactor is in fluid communication with the inlet conduit and the outlet conduit (Step 808); cultivating the biomass using the first photobioreactor (Step 810); anchoring the vertical stack to the ocean floor via a mooring system (Step 812); receiving the biomass from the outlet conduit at the mooring system (Step 814); and outputting the biomass to a harvest pipeline (Step 816).

Elements or steps of different implementations described may be combined to form other implementations not specifically set forth previously. Elements or steps may be left out of the systems or processes described previously without adversely affecting their operation or the operation of the system in general. Furthermore, various separate elements or steps may be combined into one or more individual elements or steps to perform the functions described in this specification.

Other implementations not specifically described in this specification are also within the scope of the following claims.

What is claimed is:

1. A deepwater photobioreactor system comprising:
    a vertical stack extending from an ocean floor toward an ocean surface, the vertical stack including an inlet conduit and an outlet conduit, the inlet conduit arranged to transport at least seawater, the outlet conduit arranged to transport at least a biomass;
    a first photobioreactor in fluid communication with the inlet conduit and the outlet conduit and being connected to the vertical stack via first ports in the inlet and outlet conduits at a first position along the vertical stack below the ocean surface, the first photobioreactor being arranged to cultivate a first portion of the biomass;
    a second photobioreactor in fluid communication with the inlet conduit and the outlet conduit and being connected to the vertical stack via second ports in the inlet and outlet conduits at a second position along the vertical stack at a depth below the first photobioreactor, the second photobioreactor being arranged to cultivate a second portion of the biomass; and a mooring base, connected to the bottom of the vertical stack and adjacent to the ocean floor, configured to link the outlet conduit to a seafloor pipeline and configured to anchor the vertical stack to the ocean floor.

2. The deepwater photobioreactor system of claim 1, wherein the first photobioreactor is at least 100 feet below the ocean surface.

3. The deepwater photobioreactor system of claim 1, wherein the vertical stack includes a stack housing positioned at the top of the vertical stack, the stack housing containing at least one pump arranged to move at least one of the seawater and the biomass through the inlet and outlet conduits.

4. The deepwater photobioreactor system of claim 1, wherein the first photobioreactor is oriented horizontally.

5. The deepwater photobioreactor system of claim 4, wherein the first photobioreactor includes a vessel configured to provide a unidirectional flow of biomass through the first photobioreactor along a unidirectional flow path.

6. The deepwater photobioreactor system of claim 5, wherein the first photobioreactor includes a plurality of flow generators being oriented to promote unidirectional flow to the biomass through the vessel.

7. The deepwater photobioreactor system of claim 5, wherein the first photobioreactor includes a plurality of flow generators oriented to promote biomass flow from a forward area to aft area of the vessel and a recirculator to promote biomass flow from the aft area to the forward area.

8. The deepwater photobioreactor system of claim 5, wherein the first photobioreactor includes a plurality of light sources positioned along the unidirectional flow path.

9. The deepwater photobioreactor system of claim 8, wherein the plurality of light sources include a plurality of LEDs.

10. A method for cultivating a biomass using a deepwater photobioreactor system comprising:
    extending a vertical stack from an ocean floor toward an ocean surface, the vertical stack including an inlet conduit and an outlet conduit;
    transporting at least seawater via the inlet conduit;
    transporting at least the biomass via the outlet conduit;
    connecting a first photobioreactor at a first position along the vertical stack below the ocean surface via first ports in the inlet and outlet conduits, the first photobioreactor being in fluid communication with the inlet conduit and the outlet conduit;
    connecting a second photobioreactor at a second position along the vertical stack at a depth below the first photobioreactor via second ports in the inlet and outlet conduits, the second photobioreactor being in fluid communication with the inlet conduit and the outlet conduit;
    cultivating a first portion of the biomass using the first photobioreactor and a second portion of the biomass using the second photobioreactor;
    anchoring the vertical stack to the ocean floor via a mooring base connected to the bottom of the vertical stack;
    linking the outlet conduit to a seafloor pipeline; and
    outputting the first and second portions of the biomass from the outlet conduit to the seafloor pipeline.

11. The method of claim 10 comprising positioning the first photobioreactor at least 100 feet below the ocean surface.

12. The method of claim 10, wherein the vertical stack includes a stack housing positioned at the top of the vertical stack, the stack housing containing at least one pump arranged to move at least one of the seawater and the biomass through the inlet and outlet conduits.

13. The method of claim 10 comprising orienting the first photobioreactor horizontally.

14. The method of claim 13 comprising providing a unidirectional flow of the biomass through a vessel of the first photobioreactor.

15. The method of claim 14 comprising providing a plurality of flow generators in the first photobioreactor and orienting the plurality of flow generators to promote unidirectional flow of the biomass through the vessel.

16. The method of claim 14 comprising providing a plurality of flow generators in the first photobioreactor oriented to promote biomass flow from a forward area to aft area of the vessel and a providing a recirculator to promote biomass flow from the aft area to the forward area.

17. The method of claim 14 comprising providing light in the first photobioreactor via a plurality of light sources positioned along the unidirectional flow path.

18. The method of claim 17, wherein the plurality of light sources include a plurality of LEDs.

19. A deepwater photobioreactor system comprising:
    a vertical stack extending from an ocean floor toward an ocean surface, the vertical stack including an inlet conduit and an outlet conduit, the inlet conduit arranged to transport at least seawater, the outlet conduit arranged to transport at least a biomass;
    a first photobioreactor in fluid communication with the inlet conduit and the outlet conduit and being connected to the vertical stack via first ports in the inlet and outlet conduits at a first position along the vertical stack below the ocean surface, the first photobioreactor arranged to cultivate the biomass, the first photobioreactor including at least one sensor arranged to generate sensor data based on at least one detected environmental condition;
    a second photobioreactor in fluid communication with the inlet conduit and the outlet conduit and being connected to the vertical stack via second ports in the inlet and outlet conduits at a second position along the vertical stack at a depth below the first photobioreactor, the second photobioreactor being arranged to cultivate a second portion of the biomass;
    a mooring base, connected to the bottom of the vertical stack and adjacent to the ocean floor, configured to link the outlet conduit to a seafloor pipeline and configured to anchor the vertical stack to the ocean floor; and
    a controller arranged to receive the sensor data and adjust environmental conditions by at least one of opening, closing, turning on, turning off, adjusting flow rate, adjusting mixing rate of one or more components of the first photobioreactor and/or adjusting light intensity of at least one light source of the first photobioreactor.

\* \* \* \* \*